US008679758B2

(12) United States Patent
Matsuzaki et al.

(10) Patent No.: US 8,679,758 B2
(45) Date of Patent: *Mar. 25, 2014

(54) COMPLEXITY MANAGEMENT OF GENOMIC DNA

(75) Inventors: Hajime Matsuzaki, Palo Alto, CA (US); Xing Su, Cupertino, CA (US); Sean Walsh, Danville, CA (US); Giulia Kennedy, San Francisco, CA (US); Rui Mei, Santa Clara, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,111

(22) Filed: Aug. 6, 2012

(65) Prior Publication Data

US 2013/0137583 A1    May 30, 2013

Related U.S. Application Data

(60) Continuation of application No. 13/216,893, filed on Aug. 24, 2011, now abandoned, which is a division of application No. 11/874,858, filed on Oct. 18, 2007, now Pat. No. 8,029,999, which is a division of application No. 10/264,945, filed on Oct. 4, 2002, now Pat. No. 7,297,778, which is a continuation-in-part of application No. 09/916,135, filed on Jul. 25, 2001, now abandoned.

(51) Int. Cl.
*C12Q 1/68* (2006.01)
*C07H 21/04* (2006.01)

(52) U.S. Cl.
USPC ........................................ 435/6.12; 536/24.31

(58) Field of Classification Search
None
See application file for complete search history.

(56) References Cited

U.S. PATENT DOCUMENTS

| 5,409,818 | A | 4/1995 | Davey et al. |
| 5,426,142 | A | 6/1995 | Rosano et al. |
| 5,437,990 | A | 8/1995 | Burg et al. |
| 5,565,340 | A | 10/1996 | Chenchik et al. |
| 5,604,097 | A | 2/1997 | Brenner |
| 5,624,825 | A | 4/1997 | Walker et al. |
| 5,691,136 | A | 11/1997 | Lupski et al. |
| 5,712,127 | A | 1/1998 | Malek et al. |
| 5,716,785 | A | 2/1998 | Van Gelder et al. |
| 5,759,822 | A | 6/1998 | Chenchik et al. |
| 5,763,239 | A | 6/1998 | Short et al. |
| 5,871,697 | A | 2/1999 | Rothberg et al. |
| 6,040,138 | A | 3/2000 | Lockhart et al. |
| 6,107,023 | A | 8/2000 | Reyes et al. |
| 6,110,711 | A | 8/2000 | Serafini et al. |
| 6,114,152 | A | 9/2000 | Serafini et al. |
| 6,207,372 | B1 | 3/2001 | Shuber |
| 6,207,379 | B1 | 3/2001 | Lee et al. |
| 6,277,606 | B1 | 8/2001 | Wigler et al. |
| 6,872,529 | B2 | 3/2005 | Su |
| 6,958,225 | B2 | 10/2005 | Dong |
| 7,214,490 | B2 * | 5/2007 | Su et al. ............... 435/6.12 |
| 8,029,999 | B2 * | 10/2011 | Matsuzaki et al. ....... 435/6.12 |

FOREIGN PATENT DOCUMENTS

| EP | 224126 A2 | 6/1987 |
| WO | WO90/08821 | 8/1990 |
| WO | WO91/05861 | 5/1991 |
| WO | WO 00/24939 * | 5/2000 |
| WO | WO01/751632 A2 | 10/2001 |
| WO | WO02/20844 A1 | 3/2002 |

OTHER PUBLICATIONS

Bernd W. Kalisch, et al., Gene: "An International Journal Focusing on Gene Cloning and Gene Structure and Function", Department of Medical Biochemistry, Faculty of Medicine, University of Calcary, Calgary, Alberta T2N 4N1 (Canada), pp. 263-270.

Dmitry A. Shagin, et al., "Regulation of Average Length of Complex PCR Product", Nucleic Acids Research, 1999 , vol. 27, No. 18, © 1999 Oxford University Press, Institute of Bioorganic Chemistry, Miklukho-Maklaya 16/11, 117871 Moscow, Russia, Received Jun. 8, 1999; Revised and Accepted Jul. 23, 1999, 3 pp.

K.A. Lukyanov, et al., "Inverted Terminal Repeats Permit the Average Length of Amplified DNA Fragments to be Regulated During Preparation of cDNA Libraries by Polymerase Chain Reaction", Analytical Biochemistry 198-202 (1995), Copyright © 1995 by Academic Press, Inc.

Kenneth H. Roux and Pushparani Dhanarajan, "A Strategy for Single Site PCR Amplification of dsDNA: Priming Digested Cloned on Genomic DNA from an Anchor-Modified Restriction Site and a Short Internal Sequence", BioTechniques, vol. 8, No. 1 (1990), 7 pp.

* cited by examiner

*Primary Examiner* — Prabha Chunduru
(74) *Attorney, Agent, or Firm* — Affymetrix, Inc.

(57) ABSTRACT

The presently claimed invention provides for novel methods and kits for analyzing a collection of target sequences in a nucleic acid sample. A sample is amplified under conditions that enrich for a subset of fragments that includes a collection of target sequences. The invention further provides for analysis of the above sample by hybridization to an array, which may be specifically designed to interrogate the collection of target sequences for particular characteristics, such as, for example, the presence or absence of one or more polymorphisms.

9 Claims, 5 Drawing Sheets

| Rest Enzyme | 400 to 800 bp | % 400 to 800 | No Gaps |
|---|---|---|---|
| Eco RI | 32908 | 5.2% | 632078 |
| Xba I | 32349 | 5.1% | 631415 |
| Pst I | 32266 | 4.9% | 659081 |
| Bgl II | 29829 | 4.8% | 627495 |
| Hind III | 19409 | 3.1% | 635752 |
| Nsi I | 17718 | 2.7% | 649122 |
| Pvu II | 17150 | 2.6% | 653501 |
| Bsr GI | 13923 | 2.2% | 626285 |
| Nco I | 13290 | 2.2% | 610472 |
| Bcl I | 11212 | 1.8% | 616261 |
| Sac I | 9246 | 1.6% | 579210 |
| Apa I | 8170 | 1.6% | 524802 |
| Apa LI | 4978 | 0.9% | 556948 |
| BamHI | 3136 | 0.6% | 535953 |
| Kpn I | 1633 | 0.3% | 505444 |
| Xho I | 417 | 0.1% | 516532 |
| Bsp EI | 350 | 0.1% | 547247 |
| Sal I | 58 | 0.0% | 683138 |
| Top 4 | 127352 | | |

SEQUENCE LISTING

<160> NUMBER OF SEQ ID NOS: 1

<210> SEQ ID NO 1
<211> LENGTH: 490
<212> TYPE: DNA
<213> ORGANISM: Homo Sapiens

<400> SEQUENCE: 1

```
aagcttcagt aatggtggac gcttctcctg ccacaaagct ccaacgtccc aggtcgaccc      60
cagactgctg tgctcgcggt gagaatttca agccagtggg tcttagcttg ctgggctcca     120
tgggggtggg atctgcttag ctagaccact tgactccctg gcttcagccc cctttccagg     180
ggagtgaatg gttctgtctt gctggtgttc taggtgccac tggggtatga aaaaaactcc     240
tgcagctagc aggaccagat gtattcacag ctgaattcta ccagaggtac aaagaggagc     300
cggtactgtt ccttctgaaa ctatttcaaa caatagaaaa aaagggactc ctccctaatg     360
cattttatga ggccagcatc atcctgatac caaaacctgg cagagacaca acaaaaaaag     420
aaaacttcaa gccaatgtcc ctgataaata ttgatgcgaa aatcctcaat aaaatactgg     480
cacactaaat                                                            490
```

COMPLEXITY MANAGEMENT OF GENOMIC DNA

RELATED APPLICATIONS

The present application is a continuation of application Ser. No. 13/216,893 filed Aug. 24, 2011, which is a divisional of application Ser. No. 11/874,858 filed Oct. 18, 2007, which is a divisional of application Ser. No. 10/264,945 filed Oct. 4, 2002, which is a continuation-in part of application Ser. No. 09/916,135 filed Jul. 25, 2001. All of the priority applications are incorporated by reference in their entirety for all purposes.

FIELD OF THE INVENTION

The invention relates to enrichment and amplification of sequences from a nucleic acid sample. In one embodiment, the invention relates to enrichment and amplification of nucleic acids for the purpose of further analysis. The present invention relates to the fields of molecular biology and genetics.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3\times10^9$ base pairs. Novel methods of sample preparation and sample analysis that reduce complexity may provide for the fast and cost effective exploration of complex samples of nucleic acids, particularly genomic DNA.

Single nucleotide polymorphisms (SNPs) have emerged as the marker of choice for genome wide association studies and genetic linkage studies. Building SNP maps of the genome will provide the framework for new studies to identify the underlying genetic basis of complex diseases such as cancer, mental illness and diabetes. Due to the wide ranging applications of SNPs there is still a need for the development of robust, flexible, cost-effective technology platforms that allow for scoring genotypes in large numbers of samples.

SUMMARY OF THE INVENTION

In one embodiment a method of reducing the complexity of a first nucleic acid sample to produce a second nucleic acid sample is disclosed. The method comprises first selecting a collection of target sequences by a method comprising: identifying fragments that are in a selected size range when a genome is digested with a selected enzyme or enzyme combination; identifying sequences of interest present on the fragments in the selected size range; and selecting as target sequences fragments that are in the selected size range and comprise a sequence of interest. The first nucleic acid sample is fragmented to produce sample fragments and at least one adaptor is ligated to the sample fragments. A second nucleic acid sample is generated by amplifying the sample. The amplified sample is enriched for a subset of the sample fragments and that subset included a collection of target sequences. In one embodiment the subset of sample fragments is targeted for enrichment by selecting the method of fragmentation.

In one embodiment amplification of the sample is by PCR using 20 to 50 cycles. A single primer complementary to the adaptor may be used in some embodiments. In some embodiments two different adaptors are ligated to the fragments and two different primers are used for amplification. In yet another embodiment a single adaptor is used but the adaptor has a double stranded region and single stranded regions. Primers to the single stranded regions are used for amplification. In one embodiment the adaptor sequence comprises a priming site. In another embodiment the adaptor comprises a tag sequence.

In one embodiment the step of fragmenting the first nucleic acid sample is by digestion with at least one restriction enzyme. The restriction enzyme may, for example, have a 6 base recognition sequence or an 8 base recognition sequence. In some embodiments a type IIs endonuclease is used. In one embodiment fragmenting, ligating and amplifying steps are done in a single tube.

In one embodiment the second nucleic acid sample comprises at least 0.01%, 0.5%, 3%, 12% or 50% of the first nucleic acid sample. The first nucleic acid sample may be, for example, genomic DNA, DNA, cDNA derived from RNA or cDNA derived from mRNA.

In one embodiment the target sequences are 800, 1000, 1200, 1500, or 2000 base pairs long or less. In one embodiment the subset of sample fragments enriched in the second nucleic acid sample is comprised of fragments that are primarily 2000 or 3000 base pairs long or less.

In one embodiment target sequences contain one or more sequence of interest, such as, for example, sequence variations, such as SNPs. In some embodiments a SNP may be associated with a phenotype, a disease, the efficacy of a drug or with a haplotype.

In another embodiment a method for selecting a collection of target sequences is disclosed. The steps of the method are identifying fragments that are in a selected size range when a genome is digested with a selected enzyme or enzyme combination; identifying sequences of interest present on the fragments in the selected size range; and selecting as target sequences fragments that are in the selected size range and comprise a sequence of interest. In one embodiment a computer system is used for one or more steps of the method. In one embodiment an array is designed to interrogate one or more specific collections of target sequences. In another embodiment a collection of target sequences is disclosed. The collection may be amplified. The collection may also be attached to a solid support.

In another embodiment a method is disclosed for analyzing a collection of target sequences by providing a nucleic acid array; hybridizing the amplified collection of target sequences to the array; generating a hybridization pattern resulting from the hybridization; and analyzing the hybridization pattern. In one embodiment the array is designed to interrogate sequences in the collection of target sequences. In one embodiment the sequences are analyzed to determine if they contain sequence variation, such as SNPs.

In another embodiment a method for genotyping an individual is disclosed. A collection of target sequences comprising a collection of SNPs is amplified and hybridized to an array comprising probes to interrogate for the presence or absence of different alleles in the collection of SNPs. The hybridization pattern is analyzed to determine which alleles are present for at least one of the SNPs.

In another embodiment a method for screening for DNA sequence variations in a population of individuals is disclosed. Amplified target sequences from each individual are hybridized to an array that interrogates for sequence variation. The hybridization patterns from the arrays are compared to determine the presence or absence of sequence variation in the population of individuals.

In another embodiment kits for genotyping individuals or samples are disclosed. The kit may contain one or more of the following components: buffer, nucleotide triphosphates, a reverse transcriptase, a nuclease, one or more restriction enzymes, two or more adaptors, a ligase, a DNA polymerase, one or more primers and instructions for the use of the kit. In one embodiment the kit contains an array designed to interrogate sequence variation in a collection of target sequences.

In another embodiment a solid support comprising a plurality of probes attached to the solid support is disclosed. The probes may be designed to interrogate sequence variation in a collection of target sequences.

DETAILED DESCRIPTION OF THE PREFERRED EMBODIMENTS (A) General

The present invention relies on many patents, applications and other references for details known to those of the art. Therefore, when a patent, application, or other reference is cited or repeated below, it should be understood that it is incorporated by reference in its entirety for all purposes as well as for the proposition that is recited. As used in the specification and claims, the singular form "a," "an," and "the" include plural references unless the context clearly dictates otherwise. For example, the term "an agent" includes a plurality of agents, including mixtures thereof. An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as common individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, 10, $10^{-1}$, $10^{-2}$, $10^{-3}$, $10^{-4}$, or $10^{-5}$, for example. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), all of which are herein incorporated in their entirety by reference for all purposes.

Some aspects of the present invention make use of microarrays, also called arrays. Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555. All of the above patents incorporated herein by reference in their entireties for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. patent application Ser. Nos. 10/063,559, 60/349,546, 60/376,003, 60/394,574, and 60/403,381.

The word "DNA" may be used below as an example of a nucleic acid. It is understood that this term includes all nucleic acids, such as DNA and RNA, unless a use below requires a specific type of nucleic acid.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a DNA polynucleotide, DNA or chromosome. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments distributed around a selected size range. Included in this digestion will be many fragments that are shorter than the selected range and many fragments that are longer than the selected range but many fragments will be within the selected size range. Useful size ranges may be from 1, 100, 200, 400, 700, 1000 or 2000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4^6$) base pairs while a four base pair recognition sequence will occur once every 256 ($4^4$) base pairs. In silico digestions of sequences from the Human Genome Project show that the actual occurrences may be even more infrequent for some enzymes and more frequent for others, for example, PstI cuts the human genome more often than would be predicted by this simplistic theory while SalI and XhoI cut the human genome less frequently than predicted. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes see, New England BioLabs Catalog (Beverly, Mass.) which is herein incorporated by reference in its entirety for all purposes).

Information about the sequence of a region may be combined with information about the sequence specificity of a particular restriction enzyme to predict the size, distribution and sequence of fragments that will result when a particular region of a genome is digested with that enzyme. In silico digestion is a computer aided simulation of enzymatic digests accomplished by searching a sequence for restriction sites. In silico digestion provides for the use of a computer or computer system to model enzymatic reactions in order to determine experimental conditions before conducting any actual experiments. An example of an experiment would be to model digestion of the human genome with specific restriction enzymes to predict the sizes and sequences of the resulting restriction fragments.

"Adaptor sequences" or "adaptors" are generally oligonucleotides of at least 5, 10, or 15 bases and preferably no more than 50 or 60 bases in length, however, they may be even longer, up to 100 or 200 bases. Adaptor sequences may be synthesized using any methods known to those of skill in the art. For the purposes of this invention they may, as options, comprise templates for PCR primers, restriction sites, tags and promoters. The adaptor may be partially, entirely or substantially double stranded. The adaptor may be phosphorylated or unphosphorylated on one or both strands. Modified nucleotides, for example, phosphorothioates, may also be incorporated into one or both strands of an adaptor.

Adaptors are particularly useful in some embodiments of the methods if they comprise a substantially double stranded region and short single stranded regions which are complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible.

In some embodiments the same adaptor sequence is ligated to both ends of a fragment. Digestion of a nucleic acid sample with a single enzyme may generate similar or identical overhanging or sticky ends on either end of the fragment. For example if a nucleic acid sample is digested with EcoRI both strands of the DNA will have at their 5' ends a single stranded region, or overhang, of 5'-AATT-3'. A single adaptor sequence that has a complementary overhang of 5'-AATT-3' can be ligated to each end of the fragment.

A single adaptor can also be ligated to both ends of a fragment resulting from digestion with two different enzymes. For example, if the method of digestion generates blunt ended fragments, the same adaptor sequence can be ligated to both ends. Alternatively some pairs of enzymes leave identical overhanging sequences. For example, BglII recognizes the sequence 5'-AGATCT-3', cutting after the first A, and BamHI recognizes the sequence 5'-GGATCC-3', cutting after the first G; both leave an overhang of 5'-GATC-3'. A single adaptor with an overhang of 5'-GATC-3' may be ligated to both digestion products.

When a single adaptor sequence is ligated to both ends of a fragment the ends of a single fragment may be complementary resulting in the potential formation of hairpin structures. Formation of a base pairing interaction between the 5' and 3' ends of a fragment can inhibit amplification during PCR resulting in lowered overall yield. This effect will be more pronounced with smaller fragments than with larger fragments because the probability that the ends will hybridize is higher for smaller fragments than for larger fragments.

Digestion with two or more enzymes can be used to selectively ligate separate adapters to either end of a restriction fragment. For example, if a fragment is the result of digestion with EcoRI at one end and BamHI at the other end, the overhangs will be 5'-AATT-3' and 5'-GATC-3', respectively. An adaptor with an overhang of AATT will be preferentially ligated to one end while an adaptor with an overhang of GATC will be preferentially ligated to the second end.

Methods of ligation will be known to those of skill in the art and are described, for example in Sambrook et at. and the New England BioLabs catalog both of which are incorporated herein by reference in their entireties. Methods include using T4 DNA Ligase which catalyzes the formation of a phosphodiester bond between juxtaposed 5' phosphate and 3' hydroxyl termini in duplex DNA or RNA with blunt or sticky ends; Taq DNA ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond, substrates include single-stranded RNA and DNA as well as dinucleoside pyrophosphates; or any other substrates described in the art.

A genome is all the genetic material of an organism. In some instances, the term genome may refer to the chromosomal DNA. Genome may be muitichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which is derived from chromatin and which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable, regions, mini satellites dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than $1/100$ or $1/1000$ members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

The term "target sequence", "target nucleic acid" or "target" refers to a nucleic acid of interest. The target sequence may or may not be of biological significance. Typically, though not always, it is the significance of the target sequence which is being studied in a particular experiment. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc. In many embodiments a collection of target sequences is identified and assayed.

A sequence may be selected to be a target sequence if it has a region of interest and shares a characteristic with at least one other target sequence that will allow the two or more target sequences to be enriched in a subset of fragments. The region of interest may be, for example, a single nucleotide polymorphism and the shared characteristic may be, for example, that the target sequence is found on a fragment in a selected size range when a genomic sample is fragmented by digestion with a particular enzyme or enzyme combination. Collections of target sequences that each have a region of interest and share a common characteristic are particularly useful. For example, a collection of target sequences that each contain a location that is known to be polymorphic in a population and are each found on a fragment that is between 400 and 800 base pairs when human genomic DNA is digested with XbaI may be interrogated in a single assay. A collection may comprise from 2, 100, 1,000, 5,000, 10,000, or 50,000 to 1,000, 5,000, 10,000, 20,000, 50,000, 100,000, 1,000,000 or 3,500,000 different target sequences.

The term subset of fragments or representative subset refers to a fraction of a genome. The subset may be less than or about 0.01, 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

Target sequences may be interrogated by hybridization to an array. The array may be specially designed to interrogate one or more selected target sequence. The array may contain a collection of probes that are designed to hybridize to a region of the target sequence or its complement. Different probe sequences are located at spatially addressable locations on the array. For genotyping a single polymorphic site probes that match the sequence of each allele may be included. At least one perfect match probe, which is exactly complementary to the polymorphic base and to a region surrounding the polymorphic base, may be included for each allele. Multiple perfect match probes may be included as well as mismatch probes.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991), each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix (Santa Clara, Calif.) under the brand name GeneChip® and are directed to a variety of purposes, including genotyping and gene expression monitoring for a variety of eukaryotic and prokaryotic species.

Hybridization probes are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. See U.S. patent application Ser. No. 08/630,427.

Hybridizations are usually performed under stringent conditions, for example, at a salt concentration of no more than 1M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al. which is hereby incorporated by reference in its entirety for all purposes above.

An individual is not limited to a human being, but may also include other organisms including but not limited to mammals, plants, fungi, bacteria or cells derived from any of the above.

(C.) Preferential Amplification of a Subset of Fragments Containing Target Sequences The present invention provides for novel methods of analysis of a nucleic acid sample, such as genomic DNA. The methods include: identification and selection of a collection of target sequences; amplification of a selected subset of fragments that comprises a collection of target sequences; and, analysis of a collection of target sequences. In many embodiments a subset of fragments may be amplified by PCR wherein the subset of fragments that is amplified efficiently is dependent on the size of the fragments. In one embodiment fragmentation conditions and target sequences are selected so that the target sequences are present in the subset of fragments that are efficiently amplified by PCR. Those fragments that are efficiently amplified are enriched in the amplified sample and are present in amounts sufficient for hybridization analysis and detection using the methods disclosed. Many fragments will not be amplified efficiently enough for detection using the methods disclosed and these fragments are not enriched in the amplified sample.

In many embodiments the methods include the steps of: identifying a collection of target sequences that carry sequences of interest on fragments of a selected size range; fragmenting a nucleic acid sample by digestion with one or more restriction enzymes so that the target sequences are present on fragments that are within the selected size range; ligating one or more adaptors to the fragments; and amplifying the fragments so that a subset of the fragments, including fragments of the selected size range, are enriched in the amplified product. In some embodiments the amplified sample is exposed to an array which may be specifically designed and manufactured to interrogate one or more target sequences in a collection of target sequences.

In some embodiments the selected size range is selected to be within the size range of fragments that can be efficiently amplified under a given set of amplification conditions. In many embodiments amplification is by PCR and the PCR conditions are standard PCR amplification conditions (see, for example, PCR primer A laboratory Manual, Cold Spring Harbor Lab Press, (1995) eds. C. Dieffenbach and G. Dveksler), under these conditions fragments that are of a predicted size range, generally less than 2 kb, will be amplified most efficiently.

Figure 1:
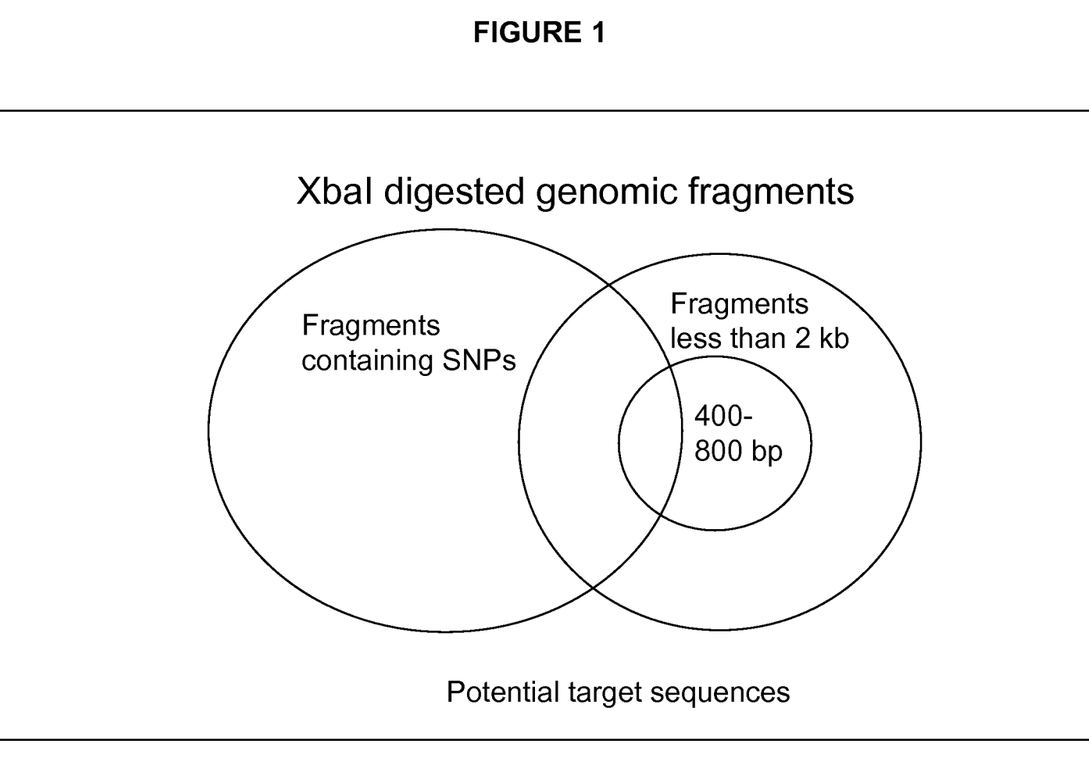
FIG. 1 shows a Venn diagram illustrating how a collection of target sequences may be selected. Potential target sequences are found at the intersection between the set of fragments that contain sequences of interest and the fragments that are in a selected size range. The selected size range is within the set of fragments that are efficiently amplified by PCR under standard conditions.

FIG. 1 illustrates an example of how possible target sequences may be defined. The starting set is all of the fragments of the genome following fragmentation. Within this set there is a subset of fragments that are about 2 kb and less and would be efficiently amplified by PCR under standard conditions. Also within the starting set is a subset of fragments that contain sequences of interest, for example, fragments that contain SNPs. There is an intersection between these two subsets that represents fragments that will be efficiently amplified under standard PCR conditions and contain sequences of interest. In one embodiment these fragments are possible target sequences. In some embodiments a smaller subset is selected from within the subset of fragments that are about 2 kb and less. This subset may be, for example, fragments from about 1, 100, 200, or 400 bp to 600, 800, 1,200, 1,500 or 2,000 bp. The intersection of this subset with the subset of fragments that comprise a sequence of interest contains fragments that are potential target sequences. The set of potential target sequences will vary depending on the fragmentation method used and the size range that is selected. The collection of target sequences may comprise all potential target sequences or a further subset of the possible target sequences. Potential target sequences may be selected for the collection of target sequences or removed from the collection of target sequences based on secondary considerations such as performance in hybridization experiments, location in the genome, proximity to another target sequence in the collection, association with phenotype or disease or any other criteria that is known in the art. Additional selection criteria that may be used to select target sequences for a collection of target sequences also include, for example, clustering characteristics, whether or not a SNP is consistently present in a population, Mendelian inheritance characteristics, Hardy-Weinberg probability, and chromosomal map distribution. In one embodiment fragments that contain repetitive sequences, telomeric regions, centromeric regions and heterochromatin domains may be excluded. In one embodiment the target sequences comprise SNPs and the SNPs are selected to provide an optimal representation of the genome. For example SNPs may be selected so that the distance between SNPs in the target collection is on average between 10, 50, 100, 200 or 300 and 50, 100, 200, 400, 600 or 800 kb. Inter-SNP distances may vary from chromosome to chromosome. In one embodiment more than 80% of the SNPs in the collection of target sequence are less than about 200 kb from another SNP in the collection of target sequences. In another embodiment more than 80% of the SNPs are less than about 10, 50, 100, 150, 300 or 500 kb from another SNP in the collection of target sequences. In one embodiment SNPs that give errors across multiple families are not selected for the collection of SNPs or are removed from the analysis. In another embodiment SNPs that give ambiguous results in multiple experiments are not selected for the collection of SNPs or are removed from the analysis.

In many embodiments the methods employ the use of a computer system to assist in the identification of potential target sequences or in the selection of target sequences for a collection. For many organisms, including yeast, mouse, human and a number of microbial species, a complete or complete draft of the genomic sequence is known and publicly available. Knowledge of the sequences present in a nucleic acid sample, such as a genome, allow prediction of the sizes and sequence content of fragments that will result when the genome is fragmented under selected conditions. The pool of predicted fragments may be analyzed to identify which fragments are within a selected size range, which fragments carry a sequence of interest and which fragments have both characteristics. In some embodiments an array may then be designed to interrogate at least some of those potential target sequences. A nucleic acid sample may then be digested with the selected enzyme or enzyme and amplified under the selected amplification conditions, resulting in the amplification of the collection of target sequences. The amplified target sequences may then be analyzed by hybridization to the array. In some embodiments the amplified sequences may be further analyzed using any known method including sequencing, HPLC, hybridization analysis, cloning, labeling, etc.

Figure 2:
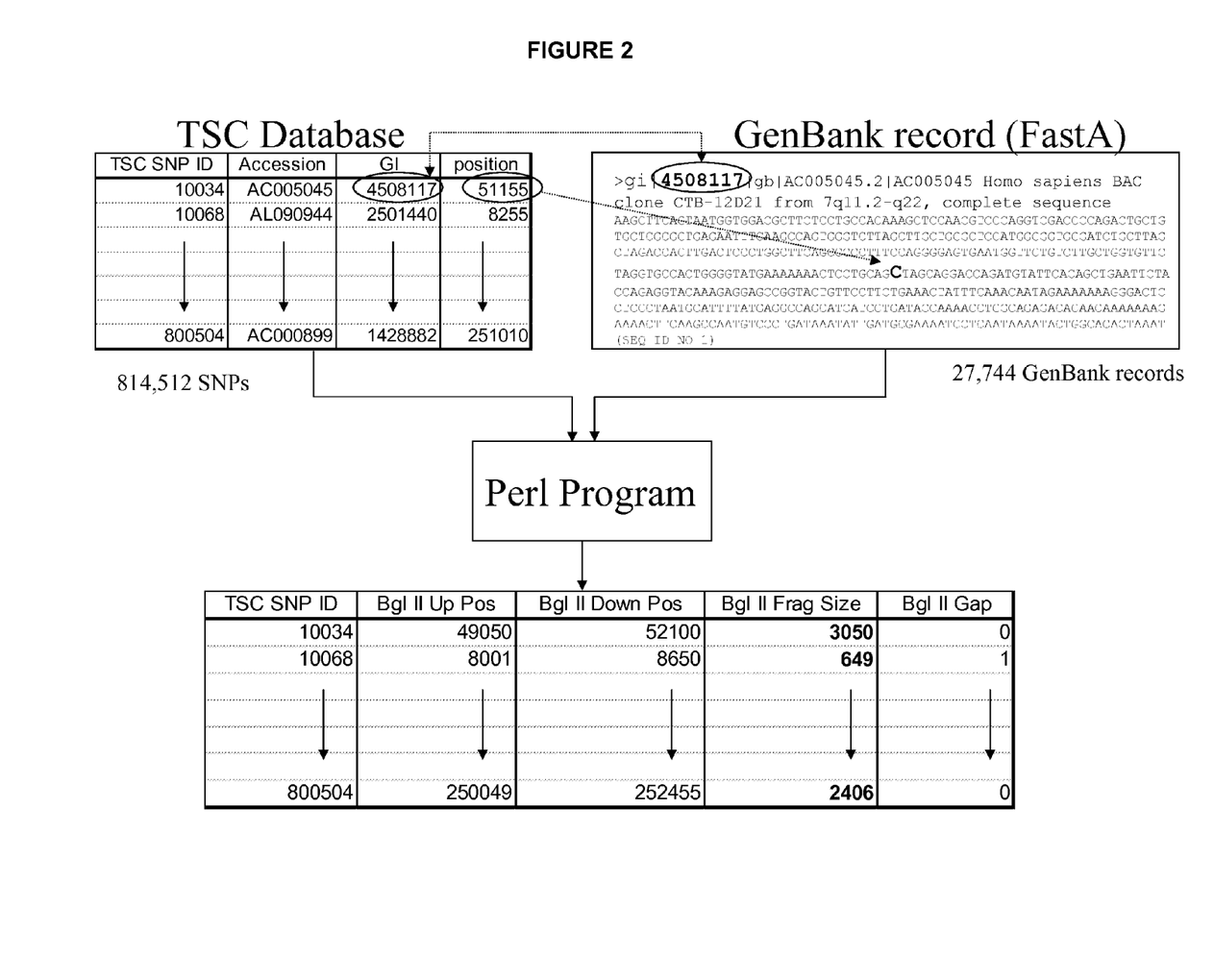
FIG. 2 shows how in silico digestion can be used to predict the size of restriction fragments containing SNPs.

In many embodiments in silico digestion techniques are used to identify one or more SNPs that will be present on fragments of a selected size when a genome is digested with a particular enzyme or enzyme combination. In FIG. 2, a computer is used to locate a SNP from a public database, for example the database provided by The SNP Consortium (TSC), or within the sequence of the human genome, for example in the publicly available database such as Genbank. A computer may then be used to predict the, for example, BglII restriction sites upstream and downstream of a given SNP. For example, in FIG. 2 TSC SNP ID 10034 has a BglII site at upstream position 49050 and a downstream BglII site at position 52100. Given these restriction sites it is predicted that SNP 10034 will be contained on a 3050 base pair fragment when human genomic DNA is digested with BglII.

The SNPs and corresponding fragment sizes may be further separated into subsets according to fragment size. In some embodiment this step is performed by a computer or computer system. In this way a computer could be used to identify all of the SNPs that are predicted to be found on fragments that are between, for example, 200, 400, 600 or 800 and 800, 1000, 1500 or 2000 base pairs in length when a sample DNA is digested with a selected enzyme or enzyme combination.

In another embodiment the SNPs present on fragments of a selected size range following fragmentation are selected as target sequences and an array is designed to interrogate at least some of the SNPs. For example, an array may be designed to genotype some of the SNPs that are present on fragments of 400 to 800 base pairs when human genomic DNA is digested with XbaI. If, for example, there are 15,000 SNPs that meet these criteria a subset of these SNP, for example, 10,000 may be selected for the array.

Figure 3:
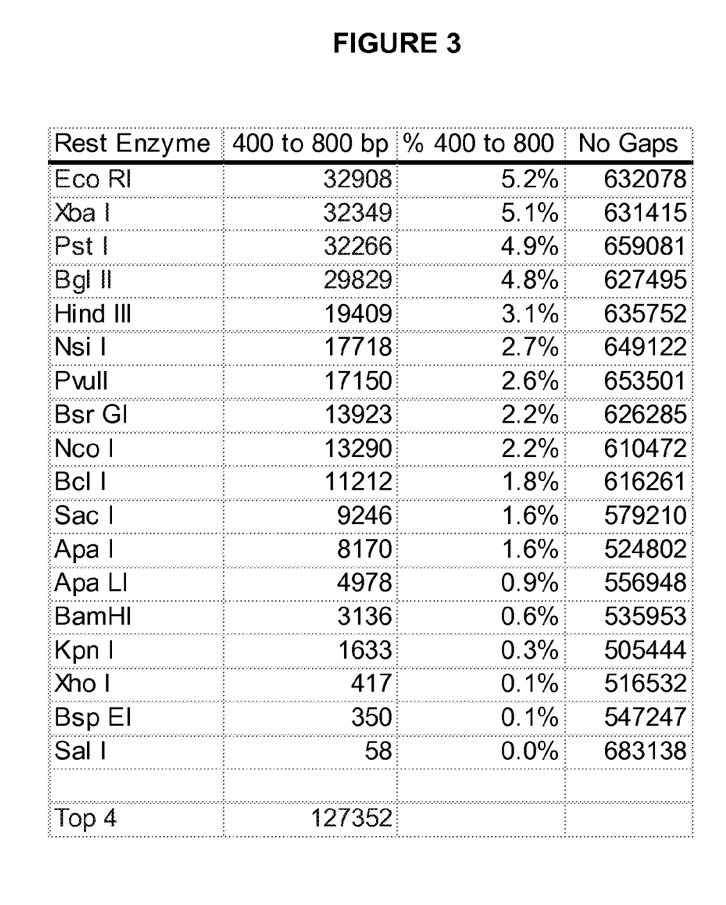
FIG. 3 is a table of the number of SNPs predicted to be found on 400 to 800 base pair fragments when genomic DNA is digested with the restriction enzyme in column 1.

In FIG. 3, in silico digestion was used to predict restriction fragment lengths for the more than 800,000 SNPs in the TSC database and to identify those SNP containing fragments between 400 and 800 base pairs. For example, when human genomic DNA is digested with EcoRI, 32,908 SNPs from the TSC database are predicted to be found on fragments between 400 and 800 base pairs. More than 120,000 of the TSC SNPs are found on fragments between 400 and 800 base pairs when genomic DNA is digested with EcoRI, XbaI, PstI and BglII.

Figure 4:
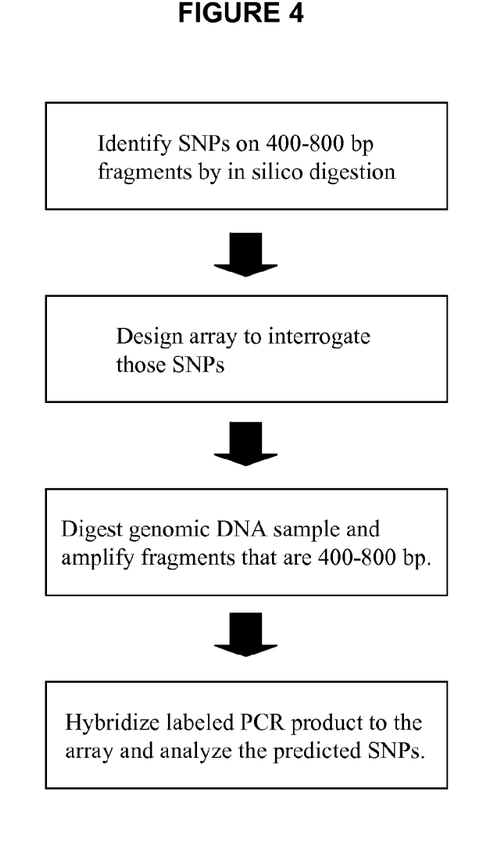
FIG. 4 is a flow chart showing design of an array in conjunction with size selection of SNP containing fragments.

In one embodiment in silico prediction of the size of SNP containing fragments is combined with selection of a collection of target sequences to design genotyping assays and arrays for genotyping, see FIG. 4. In one embodiment target sequences are selected from fragments that are those in the size range of 400 to 800 base pairs, but other size ranges could also be used for example, 100, 200, 500, 700, or 1,500 to 500, 700, 1,000, or 2,000 base pairs may also be useful size ranges.

As shown in FIG. 4, in this embodiment an array is designed to interrogate the SNPs that are predicted to be found in a size fraction resulting from digestion of the first nucleic acid sample with one or more particular restriction enzymes. For example, a computer may be used to search the sequence of a genome to identify all recognition sites for the restriction enzyme, EcoRI. The computer can then be used to predict the size of all restriction fragments resulting from an EcoRI digestion and to identify those fragments that contain a known or suspected SNP or polymorphism. The computer may then be used to identify the group of SNPs that are predicted to be found on fragments of, for example, 400-800 base pairs, when genomic DNA is digested with EcoRI. An array may then be designed to interrogate that subset of SNPs that are found on EcoRI fragments of 400-800 base pairs.

Arrays will preferably be designed to interrogate from 100, 500, 1000, 5000, 8000, 10,000, or 50,000 to 5,000, 10,000, 15,000, 30,000, 100,000, 500,000 or 1,500,000 different SNPs. For example, an array may be designed to interrogate a collection of target sequences comprising a collection of SNPs predicted to be present on 400-800 base pair EcoRI fragments, a collection of SNPs predicted to be present on 400-800 base pair BclI fragments, a collection of SNPs predicted to be present on 400-800 base pair XbaI fragments, and a collection of SNPs predicted to be present on 400-800 base pair HindIII fragments. One or more amplified subsets of fragments may be pooled prior to hybridization to increase the complexity of the sample.

In some embodiments a single size selected amplification product is suitable for hybridization to many different arrays. For example, a single method of fragmentation and amplification that is suitable for hybridization to an array designed to interrogate SNPs contained on 400-800 base pair EcoRI would also be suitable for hybridization to an array designed to interrogate SNPs contained on 400-800 base pair BamHI fragments. This would introduce consistency and reproducibility to sample preparation methods.

In some embodiments SNPs present in a collection of target sequences are further characterized and an array is designed to interrogate a subset of these SNPs. SNPs may be selected for inclusion on an array based on a variety of characteristics, such as, for example, allelic frequency in a population, distribution in a genome, hybridization performance, genotyping performance, number of probes necessary for accurate genotyping, available linkage information, available mapping information, phenotypic characteristics or any other information about a SNP that makes it a better or worse candidate for analysis.

In many embodiments a selected collection of target sequences may be amplified reproducibly from different samples or from the same sample in different reactions. In one embodiment a plurality of samples are amplified in different reactions under similar conditions and each amplification reaction results in amplification of a similar collection of target sequences. Genomic samples from different individuals may be fragmented and amplified using a selected set of conditions and similar target sequences will be amplified from both samples. For example, if genomic DNA is isolated from 2 or more individuals, each sample is fragmented under similar conditions, amplified under similar conditions and hybridized to arrays designed to interrogate the same collection of target sequences, more than 50%, more than 75% or more than 90% of the same target sequences are detected in the samples.

A given target sequence may be present in different allelic forms in a cell, a sample, an individual and in a population. In some embodiments the methods identify which alleles are present in a sample. In some embodiments the methods determine heterozygosity or homozygosity at one or more loci. In some embodiments, where SNPs are being interrogated for genotype, a genotype is determined for more than 75%, 85% or 90% of the SNPs interrogated by the array. In some embodiments the hybridization pattern on the array is analyzed to determine a genotype. In some embodiments analysis of the hybridization is done with a computer system and the computer system provides a determination of which alleles are present.

In one embodiment target sequences are selected from the subset of fragments that are less than 1,000 base pairs. An in silico digestion of the human genome may be used to identify fragments that are less than 1,000 base pairs when the genome is digested with the restriction enzyme, XbaI. The predicted XbaI fragments that are under 1,000 base pairs may be analyzed to identify SNPs that are present on the fragments. An array may be designed to interrogate the SNPs present on the fragments and the probes may be designed to determine which alleles of the SNP are present. A genomic sample may be isolated from an individual, digested with XbaI, adaptors are ligated to the fragments and the fragments are amplified. The amplified sample may be hybridized to the specially designed array and the hybridization pattern may be analyzed to determine which alleles of the SNPs are present in the sample from this individual.

In some embodiments the size range of fragments remains approximately constant, and the target sequences present in the size range vary with the method of fragmentation used. For example, if the target sequences are SNP containing fragments that are 400-800 base pairs, the fragments that meet these criteria when the human genome is digested with XbaI will be different than when the genome is digested with EcoRI, although there may be some overlap. By using a different fragmentation method but keeping the amplification conditions constant different collections of target sequences may be analyzed. In some embodiments an array may be designed to interrogate target sequences resulting from just one fragmentation condition and in other embodiments the array may be designed to interrogate fragments resulting from more than one fragmentation condition. For example, an array may be designed to interrogate the SNPs present on fragments that are less than 1,000 base pairs when a genome is digested with XbaI and the SNPs present on fragments that are less than 1,000 base pairs when a genome is digested with EcoRI.

In many embodiments an enzyme is selected so that digestion of the sample with the selected enzyme followed by amplification results in a sample of a complexity that may be specifically hybridized to an array under selected conditions. For example, digestion of the human genome with XbaI, EcoRI or BglII and amplification with PCR reduces complexity of the sample to approximately 2%. In another embodiment the sample is digested with an enzyme that cuts the genome at frequencies similar to XbaI, EcoRI or BglII, for example, SacI, BsrGI or BclI. Different complexity levels may be used. Useful complexities range from 0.1, 2, 5, 10 or 25% to 1, 2, 10, 25 or 50% of the complexity of the starting sample. In some embodiments the complexity of the sample is matched to the content on an array.

In many embodiments the target sequences are a subset that is representative of a larger set. For example, the target sequences may be 1,000, 5,000, 10,000 or 100,000 to 10,000, 20,000, 100,000, 1,500,000 or 3,000,000 SNPs that may be representative of a larger population of SNPs present in a population of individuals. The target sequences may be dispersed throughout a genome, including for example, sequences from each chromosome, or each arm of each chromosome. Target sequences may be representative of haplotypes or particular phenotypes or collections of phenotypes. For a description of haplotypes see, for example, Gabriel et al., Science, 296:2225-9 (2002), Daly et al. Nat. Genet., 29:229-32 (2001) and Rioux et al., Nat. Genet., 29:223-8 (2001), each of which is incorporated herein by reference in its entirety.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/512,300, 09/916,135, 09/920, 491, 09/910,292, and 10/013,598, which are incorporated herein by reference in their entireties.

One method that has been used to isolate a subset of a genome is to separate fragments according to size by electrophoresis in a gel matrix. The region of the gel containing fragments in the desired size range is then excised and the fragments are purified away from the gel matrix. The SNP consortium (TSC) adopted this approach in their efforts to discover single nucleotide polymorphisms (SNPs) in the human genome. See, Altshuler et al., *Science* 407: 513-516 (2000) and The International SNP Map Working Group, *Nature* 409: 928-933 (2001) both of which are herein incorporated by reference in their entireties for all purposes.

PCR amplification of a subset of fragments is an alternative, non-gel-based method to reduce the complexity of a sample. PCR amplification in general is a method of reducing the complexity of a sample by preferentially amplifying one or more sequences from a complex sample. This effect is most obvious when locus specific primers are used to amplify a single sequence from a complex sample, but it is also observed when a collection of sequences is targeted for amplification.

There are many known methods of amplifying nucleic acid sequences including e.g., PCR. See, e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. Nos. 4,683,202, 4,683,195, 4,800,159, 4,965,188 and 5,333,675 each of which is incorporated herein by reference in their entireties for all purposes.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq®, AmpliTaq® Stoffel Fragment and AmpliTaq Gold® available from Applied Biosystems (Foster City, Calif.). Many are available with or without a 3- to 5' proofreading exonuclease activity. See, for example, Vent® and Vent® (exo-) available from New England Biolab (Beverly, Mass.).

Other suitable amplification methods include the ligase chain reaction (LCR) (e.g., Wu and Wallace, *Genomics* 4, 560 (1989) and Landegren et al., *Science* 241, 1077 (1988)), transcription amplification (Kwoh et al., *Proc. Natl. Acad. Sci. USA* 86, 1173 (1989)), self-sustained sequence replication (Guatelli et al., *Proc. Nat. Acad. Sci. USA*, 87, 1874 (1990)) and nucleic acid based sequence amplification (NABSA). (See, U.S. Pat. Nos. 5,409,818, 5,554,517, and 6,063,603 each of which is incorporated herein by reference in their entireties).

When genomic DNA is digested with one or more restriction enzymes the sizes of the fragments are randomly distributed over a broad range. Following adaptor ligation, all of the fragments that have adaptors ligated to both ends will compete equally for primer binding and extension regardless of size. However, standard PCR typically results in more efficient amplification of fragments that are smaller than 2.0 kb. (See Saiki et al. Science 239, 487-491 (1988) which is hereby incorporated by reference it its entirety). The natural tendency of PCR is to amplify shorter fragments more efficiently than longer fragments. This inherent length dependence of PCR results in efficient amplification of only a subset of the starting fragments. Those fragments that are smaller than 2 kb will be more efficiently amplified than larger fragments when a standard range of conditions are used. This effect may be related to the processivity of the enzyme, which limits the yield of polymerization products over a given unit of time. The polymerase may also fail to complete extension of a given template if it falls off the template prior to completion. What is observed is that longer templates are less efficiently amplified under a standard range of PCR conditions than shorter fragments. Because of the geometric nature of PCR amplification, subtle differences in yields that occur in the initial cycles will result in significant differences in yields in later cycles. (See, PCR Primer: A Laboratory Manual, CSHL Press, Eds. Carl Dieffenbach and Gabriela Dveskler, (1995), (Dieffenbach et al.) which is herein incorporated by reference in its entirety for all purposes.) Variations in the reaction conditions such as, for example, primer concentration, extension time, salt concentration, buffer, temperature, and number of cycles may alter the size distribution of fragments to some extent. Inclusion of chain terminating nucleotides or nucleotide analogs may also alter the subset of fragments that are amplified. (See, Current Protocols in Molecular Biology, eds. Ausubel et al. (2000), which is herein incorporated by reference in its entirety for all purposes.) The presence or absence of exonuclease activity may also be used to modify the subset of fragments amplified. (See, for example, *PCR Strategies*, eds. Innis et al, Academic Press (1995), (Innis et al.), which is herein incorporated by reference for all purposes).

Ligation of a single adapter sequence to both ends of the fragments may also impact the efficiency of amplification of smaller fragments due to the formation of pan-handle structures between the resulting terminal repeats, see, for example, Qureshi et al. *GATA* 11(4): 95-101, (1994), Caetano-Anolles et al. *Mol. Gen. Genet.* 235: 157-165 (1992) and Jones and Winistorfer, *PCR Methods Appl.* 2:197-203 (1993). Smaller fragments are more likely to form the pan-handle structure and the loop may be more stable than longer loops.

In some embodiments sequences that are on smaller fragments, for example, fragments less than 400 bp or less than 200 bp are not Relented as target sequences. In addition to the bias against amplification of these fragments when a single adapter is used there are also fewer small fragments following fragmentation with a restriction enzyme or enzymes. For many enzymes fragments that are, for example, smaller than 200 base pairs are relatively rare in the sample being amplified because of the infrequency of the recognition site. Since the small fragments are rare and account for relatively little sequence information there is also a decreased probability that sequences of interest will be present on small fragments.

Figure 5:
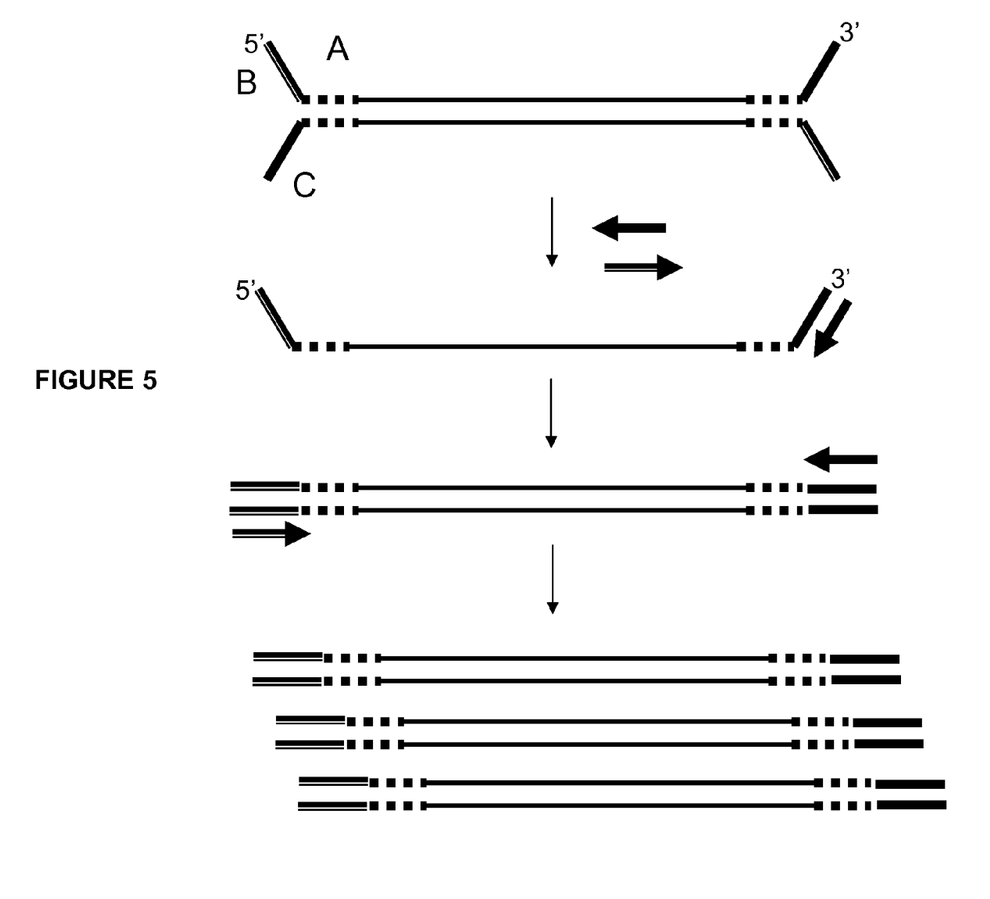
FIG. 5 is a schematic of a method in which the ends of the adaptors are non-complementary and the fragments are amplified with a primer pair.

In some embodiments the potential for formation of a stable duplex between the ends of the fragment strands is reduced. In one embodiment the adapter contains internal mismatches. In another embodiment the two strands of the adapter have a region of complementarity and a region of non-complementarity (FIG. 5). The region of complementarity (A and A') is near the end that will ligate to the fragments. The fragments can be amplified using primers to the non-complementary regions (B and C). Amplified products will have sequences B and C at the ends which will destabilize basepairing between A and A'. In another embodiment the sample may be amplified with a single primer for at least some of the cycles of amplification.

In some embodiments two or more different adaptors are ligated to the ends of the fragments. Ligation of different adaptor sequences to the fragments may result in some fragments that have the same adaptor ligated to both ends and some fragments that have two different adaptors ligated to each end. Small fragments that have different adaptors ligated to each end are more efficient templates for amplification than small fragments that have the same adaptor ligated to both ends because the potential for base pairing between the ends of the fragments is eliminated or reduced.

In one embodiment, the fragmented sample is fractionated prior to amplification by, for example, applying the sample to a gel exclusion column. Adaptors may be ligated to the fragments before or after fractionation. For example, to exclude the shortest fragments from the amplification the fragments can be passed over a column that selectively retains smaller fragments, for example fragments under 400 base pairs. The larger fragments may be recovered in the void volume. Because the shortest fragments in the PCR would be approximately 400 base pairs, the resulting PCR products will primarily be in a size range larger than 400 base pairs.

The materials for use in the present invention are ideally suited for the preparation of a kit suitable for obtaining an amplified collection of target sequences. Such a kit may comprise various reagents utilized in the methods, preferably in concentrated form. The reagents of this kit may comprise, but are not limited to, buffer, appropriate nucleotide triphosphates, appropriate dideoxynucleotide triphosphates, reverse transcriptases, nucleases, restriction enzymes, adaptors, ligases, DNA polymerases, primers, instructions for the use of the kit and arrays.

In order to interrogate a whole genome it is often useful to amplify and analyze one or more representative subsets of the genome. There may be more than 3,000,000 SNPs in the human genome, but tremendous amounts of information may be obtained by analysis of a subset of SNPs that is representative of the whole genome. Subsets can be defined by many characteristics of the fragments. In a preferred embodiment of the current invention, the subsets are defined by the proximity to an upstream and downstream restriction site and by the size of the fragments resulting from restriction enzyme digestion. Useful size ranges may be from 100, 200, 400, 700 or 1000 to 500, 800, 1500, 2000, 4000 or 10,000. However, larger size ranges such as 4000, 10,000 or 20,000 to 10,000, 20,000 or 500,000 base pairs may also be useful.

The disclosed methods may be applied to many different organisms including plants, bacteria and animals, including, human, mouse, rat, and dog. Organisms whose genomes have been sequenced are particularly useful. The genomic DNA sample may be isolated according to methods known in the art. It may be obtained from any biological or environmental source, including plant, animal (including human), bacteria, fungi or algae. Any suitable biological sample may be used for assay of genomic DNA. Convenient suitable samples include whole blood, tissue, semen, saliva, tears, urine, fecal material, sweat, buccal, skin and hair.

METHODS OF USE

The methods of the presently claimed invention can be used for a wide variety of applications including, for example, linkage and association studies, identification of candidate gene regions, genotyping clinical populations, correlation of genotype information to phenotype information, loss of heterozygosity analysis, and identification of the source of an organism or sample, or the population from which an organism or sample originates. Any analysis of genomic DNA may be benefited by a reproducible method of complexity management. Furthermore, the methods and enriched fragments of the presently claimed invention are particularly well suited for study and characterization of extremely large regions of genomic DNA.

In a preferred embodiment, the methods of the presently claimed invention are used for SNP discovery and to genotype individuals. For example, any of the procedures described above, alone or in combination, could be used to isolate the SNPs present in one or more specific regions of genomic DNA. Selection probes could be designed and manufactured to be used in combination with the methods of the invention to amplify only those fragments containing regions of interest, for example a region known to contain a SNP. Arrays could be designed and manufactured on a large scale basis to interrogate only those fragments containing the regions of interest. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, U.S. Pat. No. 6,361,947 which is herein incorporated by reference in its entirety for all purposes.

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000-2,000 bases when two human chromosomes are compared. (See, The international SNP Map Working Group, *Science* 409: 928-933 (2001) incorporated herein by reference in its entirety for all purposes.) Human diversity is limited not only by the number of SNPs occurring in the genome but further by the observation that specific combinations of alleles are found at closely linked sites.

Correlation of individual polymorphisms or groups of polymorphisms with phenotypic characteristics is a valuable tool in the effort to identify DNA variation that contributes to population variation in phenotypic traits. Phenotypic traits include physical characteristics, risk for disease, and response to the environment. Polymorphisms that correlate with disease are particularly interesting because they to represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531-537 (2001) hereby incorporated by reference in its entirety for all purposes.)

Pharmacogenomics

Pharmacogenomics refers to the study of how genes affect response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, Science 286: 487-491 (2001) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population, prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharmaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures. Paternity testing is commonly used to establish a biological relationship between a child and the putative father of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. *Nature Genet.* 22, 78 (1999)).

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual.

Marker Assisted Breeding

Genetic markers can assist breeders in the understanding, selecting and managing of the genetic complexity of animals and plants. Agriculture industry, for example, hag a great deal of incentive to try to produce crops with desirable traits (high yield, disease resistance, taste, smell, color, texture, etc.) as consumer demand increases and expectations change. However, many traits, even when the molecular mechanisms are known, are too difficult or costly to monitor during production. Readily detectable polymorphisms which are in close physical proximity to the desired genes can be used as a proxy to determine whether the desired trait is present or not in a particular organism. This provides for an efficient screening tool which can accelerate the selective breeding process.

EXAMPLES

Example 1

Digestion: Digest 300 ng human genomic in a 20 µl reaction in 1×NEB buffer 2 with 1×BSA and 1 U/µl Xba1 (NEB). Incubate the reaction at 37° C. overnight or for 16 hours. Heat inactivate the enzyme at 70° C. for 20 minutes.

Ligation: Mix the 20 μl digested DNA with 1.25 μl of 5 μM adaptor, 2.5 μl 10× ligation buffer and 1.25 μl 400 U/μl ligase. The final concentrations are 12 ng/μl DNA, 0.25 μM adaptor, 1× buffer and 20 U/μl ligase. Incubate at 16° C. overnight. Heat inactivate enzyme at 70° C. for 20 minutes. Sample may be stored at −20° C.

Amplification: Mix the 25 μl ligation reaction in a 1000 ul PCR reaction. Final concentrations of reagents are as follows: 1×PCR buffer, 250 μM dNTPs, 2.5 mM $MgCl_2$, 0.5 μM primer, 0.3 ng/μl ligated DNA, and 0.1 U/μl Taq Gold. The reaction is divided into 10 tubes of 100 μl each prior to PCR.

Reaction cycles are as follows: 95° C. for 10 minutes; 20 cycles of 95° for 20 seconds, 58° C. for 15 seconds and 72° C. for 15 seconds; and 25 cycles of 95° C. for 20 seconds, 55° C. for 15 seconds, and 72° C. for 15 seconds followed by an incubation at 72° C. for 7 minutes and then incubation at 4° C. indefinitely. Following amplification 3 μl of the sample may be run on a 2% TBE minigel at 100V for 1 hour.

Fragmentation and Labeling: PCR reactions were cleaned and concentrated using a Qiagen PCR clean up kit according to the manufacturer's instructions. Eluates were combined to obtain a sample with approximately 20 μg DNA, approximately 250-300 μl of the PCR reaction was used. The 20 μg product should be in a volume of 43 μl, if necessary vacuum concentration may be required. The DNA in 43 μl was combined with 5 μl 10×NEB buffer 4, and 2 μl 0.09 U/μl DNase and incubated at 37° C. for 30 min, 95° C. for 10 minutes then to 4° C. DNA was labeled with TdT under standard conditions.

Hybridization: Standard procedures were used for hybridization, washing, scanning and data analysis. Hybridization was to an array designed to detect the presence or absence of a collection of human SNPs present on XbaI fragments of 400 to 1,000 base pairs.

Example 2

Genomic DNA was digested with XbaI by mixing 5 μl 50 ng/μl human genomic DNA (Coriell Cell Repositories) with 10.5 μl $H_2O$ (Accugene), 2 μl 10×RE buffer 2 (NEB, Beverly, Mass.), 2 μl 10×BSA (NEB, Beverly, Mass.), and 0.5 μl XbaI (NEB, Beverly, Mass.). The reaction was incubated at 30° C. for 2 hours, then the enzyme was inactivated by incubation at 70° C. for 20 min and then to 4° C. The reaction may be stored at −20° C.

For ligation of the adapters the digested DNA was then mixed with 1.25 μl 5 uM adaptor in TE pH 8.0, 2.5 μl T4 DNA ligation buffer and 1.25 μl T4 DNA Ligase (NEB, Beverly, Mass.) which is added last. The reaction was incubated at 16° C. for 2 hours then at 70° C. for 20 min and then to 4° C. The 25 μl ligation mixture is then diluted with 75 μl $H_2O$ and may be stored at −20° C.

For PCR 10 μl of the diluted ligated DNA is mixed with 10 μl PCR buffer II (Perkin Elmer, Boston, Mass.), 10 μl 2.5 mM dNTP (PanVera Takara, Madison, Wis.), 10 μl 25 mM $MgCl_2$, 7.5 μl 10 μM primer (for a final concentration of 0.75 μM), 2 μl 5 U/μl Taq Gold (Perkin Elmer, Boston, Mass.) and 50.5 μl $H_2O$. For each array four 100 μl reactions were prepared. Amplification was done using the following program: 95° C. for 3 min; 35 cycles of 95° C. for 20 sec, 59° C. for 15 sec and 72° C. for 15 sec; and a final incubation at 72° C. for 7 min. The reactions were then held at 4° C. The lid heating option was selected.

The PCR reactions were then purified by mixing the 100 μl PCR reaction with 500 μl PB or PM buffer into Qiagen columns (Valencia, Calif.) and the column was centrifuged at 13,000 rpm for 1 min. Flow through was discarded and 750 μl PE buffer with ethanol was added into the column to wash the sample and the column was spun at 13,000 rpm for 1 min. The flow through was discarded and the column was spun at 13,000 rpm for another 1 min. The flow through was discarded and the column was placed in a new collection tube. For 2 of the 4 samples 30 μl of EB elution buffer pH 8.5 was added to the center of the QIAquick membrane to elute the sample and the columns were allowed to stand at room temperature for 5 min and then centrifuged at 13,000 for 1 min. The elution buffer from the first 2 samples was then used to elute the other 2 samples and the eluates were combined. The DNA was quantified and diluted so that 48 μl contains 20 μg DNA.

The DNA was fragmented by mixing 48 μl DNA (20 μg), 5 μl RE Buffer 4, and 2 μl 0.09 U/μl DNase in a total volume of 55 μl. The reaction was incubated at 37° C. for 30 min then 95° C. for 15 min and then held at 4° C.

Fragments were labeled by incubating 50 μl fragmented DNA, 13 μl 5×TdT buffer (Promega, Madison, Wis.), 1 μl 1 mM biotinolated-ddATP (NEN Life Sciences, Boston, Mass.), and 1 μl TdT (Promega, Madison, Wis.) at 37° C. overnight then at 95° C. for 10 min, then held at 4° C.

Hybridization mix is 12 μl 1.22 M MES, 13 μl DMSO, 13 μl 50×Denharts, 3 μl 0.5M EDTA, 3 μl 10 mg/ml herring sperm DNA, 3 μl 10 nM oligo B2, 3 μl 1 mg/ml Human Cot-1, 3 μl 1% Tween-20, and 140 μl 5M TMACL. 70 μl labeled DNA was mixed with 190 μl hybridization mix. The mixture was incubated at 95° C. for 10 min, spun briefly and held at 47.5° C. 200 μl of the denatured mixture was hybridized to an array at 47.5° C. for 16 to 18 hours at 60 rpm.

Staining mix was 990 μl $H_2O$, 450 μl 20×SSPE, 15 μl Tween-20, 30 μl 50% Denharts. For the first stain mix 495 μl staining mix with 5 μl 1 mg/ml streptavidin (Pierce Scientific, Rockford, Ill.), for the second stain mix 495 μl staining mix with 5 μl 0.5 mg/ml biotinylated anti-streptavidin antibody (Vector Labs, Burlingame, Calif.) and for the third stain mix 495 μl staining mix with 5 μl 1 mg/ml streptavidin, R-phycoerythrin conjugate (Molecular Probes, Eugene, Oreg.). Wash and stain under standard conditions.

CONCLUSION

From the foregoing it can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be to analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

We claim:

1. A method of analyzing single nucleotide polymorphisms (SNPs) comprising:
   digesting a genomic DNA to provide fragments in a size range less than 1 kb and comprising SNPs of interest;
   contacting the fragments in the size range with an array comprising probes specially designed to interrogate 10,000 to 1,500,000 SNPs on the fragments in the size range to produce a hybridization pattern; and
   analyzing the hybridization pattern to identify which alleles of the SNPs are present.

2. The method of claim 1, wherein the genomic DNA is digested with an enzyme combination.

3. The method of claim 1, wherein the array comprising probes is designed to interrogate SNPs on fragments in a size range constituting less than 1% of the complexity of the genome.

4. The method of claim 1, wherein the size range is 100-500 bases.

5. The method of claim 1, wherein more than 80% of the SNPs are less than 500 kb from another SNP.

6. The method of claim 1, wherein the array comprising probes is specifically designed to interrogate at least 10,000-500,000 SNPs on the fragments in the size range.

7. The method of claim 1, wherein the array comprising probes is specifically designed to interrogate at least 50,000 SNPs on the fragments in the size range.

8. The method of claim 1, wherein the array comprising probes is specifically designed to interrogate only SNPs on fragments in the size range.

9. The method of claim 1, wherein the genomic DNA is a human genomic DNA.

* * * * *